United States Patent [19]

Nelson

[11] Patent Number: 4,551,305
[45] Date of Patent: Nov. 5, 1985

[54] REDUCTION OF ORGANIC WASTE ODORS

[75] Inventor: Randall B. Nelson, Olympia, Wash.

[73] Assignee: International Telephone and Telegraph Corporation, New York, N.Y.

[21] Appl. No.: 544,384

[22] Filed: Oct. 21, 1983

[51] Int. Cl.⁴ .................................................. A61L 9/00
[52] U.S. Cl. .......................................... 422/5; 71/25; 162/16
[58] Field of Search ................... 162/16; 71/1, 11, 25, 71/26, 27; 422/5

[56] References Cited

U.S. PATENT DOCUMENTS

| | | | |
|---|---|---|---|
| 3,944,408 | 3/1976 | Pastrihac | 71/13 |
| 3,989,498 | 11/1976 | Cox | 71/3 |
| 4,127,383 | 11/1978 | Johnston et al. | 422/5 |
| 4,405,354 | 9/1983 | Thomas et al. | 71/21 |

OTHER PUBLICATIONS

Pulping Processes, Rydholm, 1967, pp. 539, 822, 829, 820.

*Primary Examiner*—Ferris H. Lander
*Attorney, Agent, or Firm*—James B. Raden; Harold J. Holt

[57] ABSTRACT

A formulation for the reduction of amine and ammonia odors of organic waste material comprising spent sulfite liquor containing substantially undegraded lignosulfonates and sugars, to which is added from 1 to 15%, by weight of the total solids content, of acetic acid and from 0.5 to 10 grams, per liter of formulation, of phenolic carbonyl compounds, the formulation having a pH of from 6.5 to 8.0 and preferably having being stripped of dissolved $SO_2$.

13 Claims, No Drawings

REDUCTION OF ORGANIC WASTE ODORS

This invention relates to a formulation for the reduction of amine and ammonia odors of organic waste material, to a process for the preparation of the formulation and to the use of the formulation for the reduction of such odors.

The control of amine odor associated with spent poultry litter, fish wastes and other amine or ammonia producing organic waste material is a major problem for livestock producers. Many efforts have been made to solve this and related odor problems associated with organic wastes and a number of such efforts are set forth in the literature. See, for example, the description of the prior art in the disclosure of U.S. Pat. No. 4,405,354 to Thomas et al. This prior art has included the treatment of sewage sedimentation with spent sulfite liquor (U.S. Pat. No. 3,944,408 to Postrihac) and the use of a salt of lignosulfonic acid and a foaming agent for treating amine and proteinaceous waste (U.S. Pat. No. 4,127,383 to Johnston et al). The use of glacial acetic acid and amyl alcohol as a deodorant with such optional ingredients as 2-3-butanedione or benzaldehyde is shown in U.S. Pat. No. 3,989,498 to Cox.

It has also recently been suggested that waste streams containing waste acetic acid and high lignosulfonic acid content, of the type associated with pulping operations, be used for controlling such odors. One such specific waste stream which has been suggested is vanillin black liquor containing acetic acid. Vanillin black liquor (VBL) is a waste stream resulting from the production of vanillin by the alkaline oxidation of spent sulfite liquor. Spent sulfite liquor (SSL) is itself a waste stream resulting from the pulping of wood with sulfurous acid and a bisulfite. For reasons which will become apparent from the discussion below, SSL as such, with or without the addition of acetic acid, is only partially effective for the control of amine odors. VBL is somewhat more effective for reducing amine and ammonia odors in organic wastes but it has a number of drawbacks. Because VBL is a waste stream, there is little flexibility in its formulation for different levels or types of odor control. As a waste stream, its formulation also lacks consistency. Moreover, certain of the components of VBL have not been recognized as safe for human and animal consumption. VBL normally contains contamination with heavy metals and a high salt load-both undesirable in odor control applications of the type here considered. In addition, certain of the useful odor controlling constituents of SSL are degraded in the production of vanillin and thus are present in relatively inert form in VBL.

It is accordingly a primary object of the present invention to provide an economical but effective formulation for the control of amine and ammonia odors in organic wastes.

It is an additional object of this invention to provide a formulation for such odor control which is more effective than vanillin black liquor or other waste streams containing lignosulfonates and acetic acid.

It is still an additional object of this invention to provide an effective means of controlling amine and ammonia organic waste odors utilizing a formulation containing a waste by-product which is reproducible on a consistent basis and is flexible in composition.

The foregoing and other objects of this invention are obtained in a formulation comprising spent sulfite liquor containing substantially undegraded lignosulfonates and sugars, the spent sulfite liquor containing from 1 to 15% by weight, based upon the solids content of the spent sulfite liquor, of acetic acid and from 0.5 to 10 grams per liter of solution of phenolic carbonyl compound, the formulation having a pH ranging from 6.5 to 8.0. The formulation is prepared by adding acetic acid and phenolic carbonyl compound to the aforesaid stripped spent sulfite liquor to provide from 1.0 to 15% by weight, based upon the solids content of the spent sulfite liquor, of acetic acid and from 0.5 to 10 grams per liter of solution of phenolic carbonyl compound and adjusting the pH of said solution to the range of 6.5 to 8.0. The invention also includes the process of reducing amine and ammonia odors of organic waste material by applying the aforesaid solution to the waste material. The formulation is preferably stripped of dissolved $SO_2$.

The invention is in part based upon an understanding of the function of the various critical constituents of the formulation and is believed to involve the following considerations. VBL, which as previously indicated, is somewhat effective with acetic acid for reducing odors in organic wastes, consists of extensively desulfonated, degraded lignin condensation products with degraded sugar fragments and residual vanillin type phenolic aldehydes and ketones, normally about 2 grams per liter of vanillin or vanillin-type compounds. I have found that the active constituent in VBL which acts to scavenge the amines and thus reduce odors in organic waste is the residual lignin-derived aldehydes and ketones (vanillin, acetovanillone, etc . . . ). The function of the acetic acid is to tie up some of the amines as acetate salts and to act as a catalyst in the formation of a Schiff base intermediate from vanillin:

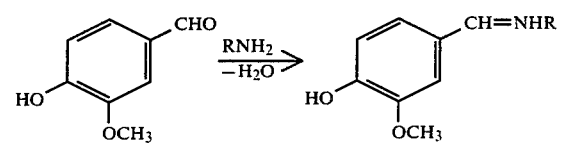

The resulting Schiff base probably reacts with another mole of amine to form a hemiaminal:

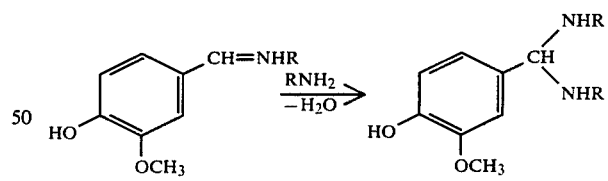

On the other hand, SSL as such contains some acetic acid but no phenolic carbonyl compounds—i.e., no lignin-derived aldehydes and ketones. These are formed essentially only by the hydrolytic breakdown of the lignin molecules. SSL does however contain reactive substantially undegraded sugars. The sugars comprise more than 15%, generally 20%, by weight (on a dry basis) of the SSL. These sugars are reactive with amines and bind them chemically. In addition, the lignin portions of the SSL in the formulations of the invention have several sites which are capable of binding amine molecules. In VBL, the excess $Na_2SO_4$ salt load and the excess caustic as well as the degraded sugars and lignin products possibly have some dispersant activity but for the most part these constituents are believed to be inert ingredients in terms of amine reactivity and odor control.

Thus, in the formulations of the invention, I start with a solution of SSL containing reactive sugars and undegraded lignin molecules. I then blend with the SSL sufficient acetic acid and lignin-based phenolic aldehydes and ketones (vanillin type compounds) to provide from 1 to 15% by weight of acetic acid, preferably 1 to 5%, and from 0.5 to 10 grams per liter, preferably from 3 to 7 g/l, of phenolic carbonyl compounds. A convenient source of the phenolic carbonyl compounds is the crude mixture of vanillin type aldehydes obtained from the process stream involved in the production of vanillin by the alkaline oxidation of SSL. The phenolic carbonyl compounds (or vanillin type aldehydes) may be obtained from this cooked oxidized process stream by alcohol extraction. This is the process stream involved in the production of vanillin, prior to purification, to extract vanillin itself. Such a crude mixture of vanillin type aldehydes typically contains from about 75 to 85% of vanillin, the balance being acetovanillone, p-hydroxy benzaldehyde, 5-formylvanillin and syringaldehyde. SSL normally contains varying low levels of acetic acid and acetic acid should be added to the SSL to standardize the proportion of acetic acid at a predetermined level between 1 and 15%.

The adjustment of pH is also a critical aspect of the invention. SSL streams rarely have a pH approaching 5 and they are normally from 2 to 4.5. Amines react very slowly at low pH's because they are protonated. They are much more reactive at or near a neutral pH. Moreover, at low pH's, the amines form salts with the acids. At pH's at or above about 4.5, the amines are organically bonded to the carbons of the sugars rather than forming ionic salts with the acids. In addition, the Schiff base formation, referred to above as the probable route involved in the control of amine odors, is more favored at pH's above about 4. Accordingly, the pH of the formulations should be adjusted with caustic, or other alkaline base, to an approximately neutral pH of from 6.5 to 8, preferably from 7.0 to 7.5. The resulting formulation, essentially synthesized from a waste stream, is more effective than the previously mentioned known formulations for the control of amine odors of organic waste material, in a number of respects.

In addition to containing vanillin (or other phenolic aldehydes and ketones) and acetic acid, the formulations also contain spent sulfite liquor derived sugars and reactive lignins which bind the amines chemically. This is a major improvement over VBL, which contains essentially no sugars, in terms of amine binding capability, and contains only relatively inert degraded lignin. The formulations also contain about one fourth the amount of inactive salt load of VBL. Stripped SSL contains less than 10%, usually less than about 5% sodium or other soluble base salt, vs. about 20% in VBL. This is one of the advantages of using stripped SSL. Unstripped SSL adds to the salt load because it must be neutralized with caustic.

Another important advantage of the present formulation is that, unlike other waste stream products, the critical ingredients of the formulation are added in the precise amounts needed. The formulation is thus synthesized for greatest effectiveness. This permits tailoring the level of active aldehyde required for the level of odor in a specific application. This in turn permits a one-time application of properly formulated material in place of repeated applications of a waste stream containing imprecise proportions of active constituents. The potential for salt toxicity is of course further reduced by reducing the number of applications required. Moreover, by formulating the compositions synthetically, they can be reproduced on a consistent basis to provide a product of consistent composition. Finally, all of the components of the present formulations have been recognized as safe for human and animal consumption. VBL, for example, contains too high a salt level and, in addition, contains heavy metal contamination (from the catalytic vanillin process) which preclude this recognition.

The term "spent sulfite liquor" (SSL) which identifies the starting material from which the present compositions are prepared refers to a liquor derived from the pulping of wood with a solution containing sulfurous acid and sodium, ammonium, magnesium, calcium or potassium (soluble-base) bisulfite solution. Such spent sulfite liquors have a relatively low pH (e.g., 1.5–4.0) and the lignin contained therein is considered to be in the form of lignosulfonic acids and lignosulfonic acid salts of the soluble-base. Such liquors also contain large quantities of reducing sugars, predominantly mannose and glucose, derived through hydrolysis of the carbohydrate fraction of the wood by the acidic cooking liquor. A typical sample of a mill run, soda-base SSL has the following composition, based on the total solids content:

|  | Percent |
|---|---|
| Sodium lignosulfonate | 60.50 |
| Wood sugars: | |
| Galactose | 3.85 |
| Glucose | 4.67 |
| Mannose | 14.39 |
| Arabinose | 1.28 |
| Xylose | 3.24 |
| Inorganics and by-products (by difference) | 12.07 |
| | 100.00 |

The SSL issuing from the digester of a sulfite pulping operation is normally fed to a continuous steam stripper where a high proportion of the dissolved $SO_2$ is removed and returned to the acid making system. Such a stripping operation is well known and may be carried out in conventional fashion. It is shown, for example, in U.S. Pat. No. 2,710,254 to the present assignee. It is this stripped SSL which forms the starting material from which the present formulations are prepared. The solids content of this SSL normally ranges from 30 to 55% after the stripping operation. It is desirable for purposes of the present invention to concentrate the liquor, if necessary, so that it contains a solids content of from about 40–55%. Spent sulfite liquors, their compositions, their treatment and recovery are extensively discussed in *Pulping Processes*, Rydholm, Interscience Publishers, 1965, particularly in Chapter 11, beginning at page 764 thereof, the text of which is hereby incorporated by reference.

The phenolic aldehydes and ketones which make up the phenolic carbonyl component of the present formulations are preferably lignin derived compounds produced by the hydrolysis of SSL. As previously indicated, a convenient source of phenolic carbonyl compounds is the process stream involved in producing vanillin from SSL. However, other sources of phenolic carbonyl compounds may be used. Useful phenolic carbonyl compounds include phenolic aldehydes such as protocatechualdehyde, vanillin, syringaldehyde, p-hydroxybenzaldehyde and 5-formylvanillin; and phenolic ketones such as p-hydroxyacetophenone, acetovanillone and acetosyringone. Other phenolic carbonyl compounds may be used providing they contain an aldehyde or ketone functionality on a phenolic nucleus.

The following examples illustrate the practice of the invention. Unless otherwise indicated, all parts and percentages are by weight:

EXAMPLE 1

To a process stream of stripped spent sulfite liquor, concentrated to about a 50% solids content, was added a 2% by volume charge of glacial acetic acid to provide approximately a 5% by weight acetic acid content. The stripped SSL had a pH between 3.5 and 4.5 and was prepared as a by-product of an acid bisulfite pulping operation utilizing a hemlock chip furnish. In place of acetic acid, evaporator condensate from the SSL containing an equivalent amount of acetic acid could also have been used. The resulting solution was then treated with sufficient crude vanillin type phenolic aldehydes to provide a 5 g/l charge of aldehydes.

The crude phenolic aldehydes were obtained by alcohol extraction from a vanillin process stream and contained 79% vanillin, 11% acetovanillin, (each ±5%), 7% p-hydroxybenzaldehyde, 2% 5-formylvanillin (each ±1%) and 1% syringaldehyde (±0.5%). The resulting amber solution was stirred while the pH adjustment darkened the product to a very dark brown color and allowed the odor of vanillin to mask that of the starting SSL. The resulting product had a solids content of between 45 and 50%, based on oven dried weight of the solids.

The formulation can be used by contacting waste material with the formulation in liquid form as by spraying or by simple admixture, formulated as shown in the above example, or by further delution with water or other liquid. It can also be applied in dry or granular form by placing on a suitable solid carrier. Other methods of application will be readily apparent to those skilled in the art.

I claim:

1. A amine and ammonia odor reducing formulation, comprising:
    (a) spent sulfite liquor containing substantially undegraded lignosulfonates and sugars;
    (b) 1.0 to 15.0% by weight of acetic acid, based upon the solids content of the spent sulfite liquor;
    (c) 0.5 to 10.0 grams of phenolic carbonyl compound per liter of said reducing formulation; and
    (d) an alkaline pH-modifying substance in an amount sufficient to adjust the pH to a value of from 6.5 to 8.0.

2. The formulation of claim 1 in which the spent sulfite liquor has been substantially stripped of dissolved $SO_2$.

3. The formulation of claim 1 in which the acetic acid is present in an amount ranging from 1.0 to 5.0% by weight, based upon the solids content of the spent sulfite liquor.

4. The formulation of claim 1 in which the phenolic carbonyl compound is present in an amount ranging from 3.0 to 7.0 grams per liter of said formulation.

5. The formulation of claim 1 in which the phenolic carbonyl compound comprises vanillin.

6. The formulation of claim 1 containing less than 10% by weight soluble base salt.

7. The formulation of claim 1 having a pH value ranging from 6.5 to 7.0.

8. The formulation of claim 1 in which the phenolic carbonyl compounds are a mixture of vanillin type aldehydes obtained from the process stream for the production of vanillin from spent sulfite liquor.

9. The formulation of claim 1 comprising: stripped spent sulfite liquor which is substantially free of $SO_2$; 1.0 to 5.0% by weight acetic acid; 3.0 to 7.0 grams of phenolic carbonyl compounds; and having a pH value of from 6.5 to 7.0.

10. A process for reducing amine and ammonia odors of organic waste material, which comprises contacting said organic waste material with a reaction mixture comprising:
    (a) spent sulfite liquor containing substantially undegraded lignosulfonates and sugars;
    (b) 1.0 to 15.0% by weight of acetic acid, based upon the solids content of the spent sulfite liquor;
    (c) 0.5 to 10.0 grams of phenolic carbonyl compounds per liter of such reaction mixture; and
    (d) an alkaline pH-modifying substance in an amount sufficient to adjust the pH to a value of from 6.5 to 8.0.

11. The process of claim 10 in which the phenolic carbonyl compounds comprise a mixture of vanillin-type aldehydes obtained from the process stream for the production of vanillin from spent sulfite liquor.

12. The process of claim 10 in which the spent sulfite liquor has been substantially stripped of dissolved $SO_2$.

13. The process of claim 10 comprising contacting said organic waste material with a reaction mixture, comprising: stripped spent sulfite liquor which is substantially free of $SO_2$; 1.0 to 5.0% by weight acetic acid; 3.0 to 7.0 grams of phenolic carbonyl compounds; and having a pH value of from 6.5 to 7.0.

* * * * *